(12) United States Patent
Danziger et al.

(10) Patent No.: US 11,653,607 B2
(45) Date of Patent: May 23, 2023

(54) *GYPSOPHILA* VARIETY 'DGYPSALBBF' HAVING ACUTE INFLORESCENCE BRANCHING (71) Applicant: Danziger DAN Flower Farm, Beit Dagan (IL)

(72) Inventors: Gavriel Danziger, Beit Dagan (IL); Noam Shpayer, Beit Dagan (IL); Amir Zuker, Beit Dagan (IL)

(73) Assignee: Danziger "DAN" Flower Farm

( * ) Notice: Subject to any disclaimer, the term of this patent is extended or adjusted under 35 U.S.C. 154(b) by 65 days.

(21) Appl. No.: 17/168,021

(22) Filed: Feb. 4, 2021

(65) Prior Publication Data

US 2021/0235647 A1    Aug. 5, 2021

Related U.S. Application Data

(60) Provisional application No. 62/970,552, filed on Feb. 5, 2020.

(51) Int. Cl.
*A01H 6/30* (2018.01)
*A01H 5/02* (2018.01)

(52) U.S. Cl.
CPC .............. *A01H 6/30* (2018.05); *A01H 5/02* (2013.01)

(58) Field of Classification Search
CPC ........................................ A01H 5/02
USPC ........................................ Plt./354
See application file for complete search history.

*Primary Examiner* — Susan McCormick Ewoldt
(74) *Attorney, Agent, or Firm* — Cassandra Bright (57) ABSTRACT

The invention relates to the field of *Gypsophila paniculata*, specifically, the variety designated 'DGYPSALBBF', and its unique acute inflorescence branching. The present invention relates to plant parts, including cells and any propagative material of the new variety 'DGYPSALBBF', and use of any of the plant parts for reproducing the new variety 'DGYPSALBBF'. The present invention relates to methods using any plant parts of 'DGYPSALBBF' for the purpose of deriving additional new *Gypsophila* varieties. The present invention relates to seed, plants and plant parts produced by crossing 'DGYPSALBBF' with any other *Gypsophila* variety. The present invention also relates to methods to produce new varieties of *Gypsophila paniculata* using the variety 'DGYPSALBBF' and applying plant breeding techniques.

9 Claims, 8 Drawing Sheets
(8 of 8 Drawing Sheet(s) Filed in Color)

GYPSOPHILA VARIETY 'DGYPSALBBF' HAVING ACUTE INFLORESCENCE BRANCHING

FIELD AND BACKGROUND OF THE INVENTION

The present invention relates to a new variety of *Gypsophila paniculata* referred to as 'DGYPSALBBF' as well as to new, distinct and stable characteristics found in *Gypsophila paniculata*. The present invention relates to seeds which produce plants exhibiting this characteristic as well as, plants and plant parts produced by these seeds which have all of the morphological and physiological characteristics described herein, as well as the characteristics specific to *Gypsophila paniculata* referred to as 'DGYPSALBBF'. The present invention also relates to methods for producing these seeds and plants of *Gypsophila paniculata* exhibiting the characteristics described herein. Furthermore, the present invention relates to a method of producing progeny *Gypsophila* plants by crossing the *Gypsophila paniculata* referred to as 'DGYPSALBBF', as either the female or seed or male or pollen parent, with another *Gypsophila* plant and selecting progeny. The present invention also relates to methods to produce new varieties of *Gypsophila paniculata* using the variety 'DGYPSALBBF' in a breeding program.

*Gypsophila* is a member of the Caryophillaceae family. *Gypsophila paniculata* is a vascular land plant, native to central and eastern Europe. Of the many species of *Gypsophila*, *G. paniculata* is the only one used as a cut flower, and as such it is among the most important flower crops worldwide. *Gypsophila paniculata* has been extensively commercialized for use as a cut flower in the floristry trade. This makes *Gypsophila* an important target for the breeding of new varieties with novel characteristics. There is a demand for new varieties of *Gypsophila*.

Asexual propagation of *Gypsophila* can be performed by vegetative basal cuttings, however, propagation is also performed by sowing seeds.

The new *Gypsophila* cultivar is a product of a planned breeding program conducted by the inventors, Gavriel Danziger, Noam Shpayer and Amir Zuker in Moshav Mishmar Hashiva, Israel. The objective of the breeding program was to produce useful new *Gypsophila* varieties for cut flower production. The crossing resulting in this new variety was made during July of 2011.

A need exists for a greater variety of *Gypsophila* cultivars with a variety of inflorescence configurations. Larger flowers are also a desirable feature.

The inventor has developed the characteristic of an acute angle of the inflorescence branching to form a compact, tight inflorescence. This botanical feature has not been observed previously. A new *Gypsophila* has been developed through a controlled breeding program and exhibits unique, desirable and stable characteristics. The *Gypsophila* variety illustrated herein is referred to as 'DGYPSALBBF'.

The seed parent is the unpatented, propriety variety referred to as *Gypsophila* 'GY-7-4416'. The pollen parent is the unpatented, propriety variety referred to as *Gypsophila* 'GY-11-9988'. The new variety was discovered in July 2012 by the inventor in a group of seedlings resulting from the 2011 crossing, in a greenhouse in Moshav Mishmar Hashiva, Israel. After selection of the new variety, extensive confidential testing has been performed to determine and define the desirable characteristics of the new variety.

The parent, known as 'GY-11-9988' is a result of a designed breeding program targeted to stabilize the trait of acute angels and additional desired horticultural traits required for commercial standards. The breeding program included self-crossing (in-breeding) and selection (single seed descent) for acute angels of 4 generations resulting in a wide population of F4 seedlings from which the unpatented proprietary variety referred to as '2452' was selected. The F4 seedling population exhibited approximately 90% uniformity in the regarded trait of acute angles.

The selected genotype '2452' was used as a pollen parent and out-crossed with the seed parent 'GY-7-4416' and resulted in a segregating population in which 42% of seedlings exhibited acute angels of hybrids from which an unpatented variety referred to as '3143' was selected. The segregating population was characterized by acute angels and additional horticultural traits required for commercial standards.

The unpatented variety '3143' was back-crossed with the seed parent 'GY-7-4416' and resulted in a population homogenous to the acute angels approximately by 78% from which the pollen variety 'GY-11-9988' was selected.

The pollen parent 'GY-11-9988' was then backcrossed again with the seed parent 'GY-7-4416' and resulted in a seedlings population homogenous by approximately 86% for acute angels and further horticultural traits required for a variety to be in a commercial class. The variety DGYPSALBBF was selected from this homogenous population and resulted from a back cross conducted between seed parent 'GY-7-4416' and 'GY-11-9988'. The variety 'DGYPSALBBF' was later self-crossed and an inbred population of seedlings was characterized by approximately 90% of the germplasms exhibiting the desired trait of acute angels along with other desired horticultural traits required for commercial standards.

The new variety 'DGYPSALBBF' can be produced by sexual or asexual reproduction to produce a population of progeny plants, each of which has the combination or characteristics as herein disclosed for the new variety.

DEPOSIT INFORMATION

Seeds which are variety 'DGYPSALBBF' are deposited on Nov. 24, 2022 with the National Collection of Industrial Food and Marine Bacteria(NCIMB), Ferguson Building, Bucksburn, Aberdeen, Scotland, AB21 7 GB a Budapest Treaty recognized depository which affords permanence of the deposit, and accorded International Depository Authority Accession No. NCIMB 43695.

OBJECTS OF THE INVENTION

The following embodiments and aspects thereof are described in conjunction with system, tools and methods which are meant to be exemplary, not limiting in scope The present invention, in some embodiments thereof, relates to *Gypsophila paniculata* plants and characteristics of these plants.

*Gypsophila paniculata*, also known as 'Baby's Breath', has long been valued as a filler plant in perennial border gardens and also as a long-lasting cut flowers. 'Baby's Breath' also makes an excellent dried flower. Due to its ornamental value, attempts have been made to generate varieties of *Gypsophila paniculata* incorporating novel and improved traits to the flower industry. Thus, whilst reducing the present invention to practice, the present inventors were able, for the first time, to generate *Gypsophila paniculata* comprising a plant producing a stable uniquely acute branching angles of the flowering stem.

The present invention provides *Gypsophila* plant selections that produce lateral branches having uniquely acute angles. Flowering stems of the new variety can be used in flower bouquets as filler plant material. This characteristic distinguishes the new cultivar from typical *Gypsophila paniculata* varieties.

These and other objectives have been achieved in accordance with the present invention which are the product of a planned breeding program conducted by the inventors. One embodiment of this invention is the *Gypsophila* variety 'DGYPSALBBF' described herein. The seed parent is the *Gypsophila paniculata* line identified by code GY-7-4416 (unpatented). The seed parent is the *Gypsophila paniculata* line identified by code GY-11-9988(unpatented).

The parental cultivars have a sufficient degree of homozygosity such that the progeny of the cross are genotypically and phenotypically uniform. The new *Gypsophila paniculata* 'DGYPSALBBF' therefore can be produced by sexual reproduction by crossing the parent line to produce a population of progeny plants, each of which has the combination of characteristics as herein disclosed for the new *Gypsophila paniculata* 'DGYPSALBBF'.

Seeds which are variety 'DGYPSALBBF' and contain the unique characteristic trait of acute flowering branch angles are deposited with the National Collection of Industrial Food and Marine Bacteria(NCIMB), Ferguson Building, Bucksburn, Aberdeen, Scotland and accorded Accession Number NCIMB 43695.

Another embodiment relates to a plant produced from seeds which are *Gypsophila paniculata* 'DGYPSALBBF'.

Another embodiment relates to a plant produced by vegetative means which are *Gypsophila paniculata* 'DGYPSALBBF'. The present invention also relates to plant parts, such as pollen, seeds or inflorescence produced by *Gypsophila paniculata* 'DGYPSALBBF'.

Another embodiment relates to a method of producing seed which are *Gypsophila paniculata* 'DGYPSALBBF'.

Another embodiment also relates to a method of producing plants having all the physiological and morphological characteristics of the *Gypsophila paniculata* 'DGYPSALBBF'. comprising the steps of (a) self-pollinating *Gypsophila paniculata* 'DGYPSALBBF'. (b) harvesting seeds produced from said cross; and (c) producing plants from said harvested seeds.

The present invention also relates to producing progeny plants from the cross of *Gypsophila paniculata* 'DGYPSALBBF', as the female or male parent, with another *Gypsophila* plant, and selecting progeny plants from this cross.

The present invention also relates to producing progeny plants of *Gypsophila paniculata* 'DGYPSALBBF', by any known means of vegetative propagation.

The present invention also relates to producing progeny plants of *Gypsophila paniculata* 'DGYPSALBBF', from natural or induced mutation.

Another embodiment relates to tissue culture produced from protoplast of cells from the *Gypsophila* plant disclosed in the subject application, wherein said cells or protoplasts are produced from a plant part selected from the group consisting of pollen, ovules, embryos, protoplasts, meristematic cells, callus, leaves, anthers, cotyledons, hypcotyl, pistils, roots, root tips, flowers, seeds, petiole and stems.

Another embodiment relates to a plant or a part thereof, produced by growing *Gypsophila paniculata* 'DGYPSALBBF', wherein the plant part comprises at least one cell of *Gypsophila paniculata* 'DGYPSALBBF'.

Another embodiment relates to tissue or cell culture of regenerable cells produced from the plants of *Gypsophila paniculata* 'DGYPSALBBF'. And an *Gypsophila paniculata* plant regenerated from the tissue or cell culture of *Gypsophila paniculata* 'DGYPSALBBF'.

Another embodiment relates to a method of vegetatively propagating the plant *Gypsophila paniculata* 'DGYPSALBBF' comprising the steps of: collecting tissue or cells capable of being propagated from a plant of *Gypsophila paniculata* 'DGYPSALBBF'; cultivating said tissue or cells to obtain proliferated shoots; and rooted said shoots to obtain rooted plantlets; or cultivating said tissue or cells to obtain shoots or to obtain plantlets and a plant produced by growing the plantlets or shoots of said plant.

A further embodiment relates to a method for developing a *Gypsophila paniculata* plant in a *Gypsophila* breeding program, comprising applying plant breeding techniques comprising crossing, recurrent selection, mutation breeding, wherein said mutation breeding selects for a mutation that is spontaneous or artificially induced, backcrossing, pedigree breeding, marker enhanced selection, haploid/double haploid production, or transformation to the *Gypsophila* plant of *Gypsophila paniculata* 'DGYPSALBBF', or its parts, wherein application of said techniques results in development of an *Gypsophila paniculata* plant.

A further embodiment relates to a method of introducing a mutation into the genome of *Gypsophila paniculata* 'DGYPSALBBF', and wherein the resulting plant comprises at least one genome mutation and producing plants therefrom.

In addition to the exemplary aspects and embodiments described above, further aspects and embodiments will become apparent by study of the following descriptions.

The cultivar 'DGYPSALBBF' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'DGYPSALBBF' These characteristics in combination distinguish 'DGYPSALBBF' as a new and distinct *Gypsophila* cultivar:

1. Uniquely acute branching angles of flowering stem.
2. Uniquely large flowers of at least 12 mm on average.
3. Compact internodes
4. Strong stems.
5. Heavy harvested stem weight.
6. Long side branches.
7. Range of flower colors, white, yellow, cream, yellow-green, light-green to orange.

Parent Comparison

Plants of the new cultivar 'DGYPSALBBF' are similar to plants of the seed parent, in most horticultural characteristics, however, plants of the new cultivar 'DGYPSALBBF' differ in the following;
1. The new variety has acute branching angles of the flowering stem not found in the seed parent.
2. The new variety produces larger flowers than the seed parent.
3. 'DGYPSALBBF' is not as bright white as the seed parent.
4. Flowering stems of the new variety are strong than those of the seed parent.
5. Flowering stems of the new variety are longer than those of the seed parent.

Plants of the new cultivar 'DGYPSALBBF' are similar to plants of the pollen parent, in most horticultural characteristics, however, plants of the new cultivar 'DGYPSALBBF' differ in the following;
1. The new variety has shorter flowering branches than the pollen parent.
2. The new variety produces larger flowers than the pollen parent.

Commercial Comparison

Plants of the new cultivar 'DGYPSALBBF' can be compared to the commercial variety Gypsophila 'DGYPXLENCE. 'DGYPXLENCE' is well known in the industry as a variety producing very large flowers. These varieties are similar in most horticultural characteristics; however, 'DGYPSALBBF' differs in the following:
1. While 'DGYPXLENCE' produces a large flower, 'DGYPSALBBF' produces a larger flower.
2. 'DGYPXLENCE' produces plants with a broader branch angle.

Plants of the new cultivar 'DGYPSALBBF' can also be compared to the variety Gypsophila 'DGYPCOSMIC', USPP 29,525. These varieties are similar in most horticultural characteristics; however, 'DGYPSALBBF' differs in the following:
1. 'DGYPSALBBF' flower is larger than the flower of 'DGYPCOSMIC'.
2. 'DGYPSALBBF' produces flowering stems that are more acutely angled than those of 'DGYPCOSMIC'.
3. 'DGYPSALBBF' produces flowering stems that are more compact than those of 'DGYPCOSMIC'.

BRIEF DESCRIPTION OF THE FIGURES

The patent or application file contains at least one drawing executed in color. Copies of this patent or patent application publication with color drawings will be provided by the Office upon request and payment of the necessary fees.

The accompanying photographs in FIGS. 1 through 5 illustrate the overall appearance of the new *Gypsophila paniculata* referred to as 'DGYPSALBBF', as well as a known comparator showing the colors as true as is reasonably possible with colored reproductions of this type. Colors in the photographs may differ slightly from the color values cited in the detailed botanical description which accurately describes the color of 'DGYPSALBBF'.

The photographs were taken using conventional techniques and although colors may appear different from actual colors due to light reflectance it is as accurate as possible by conventional photographic techniques.

EXAMPLES

Figure 1:
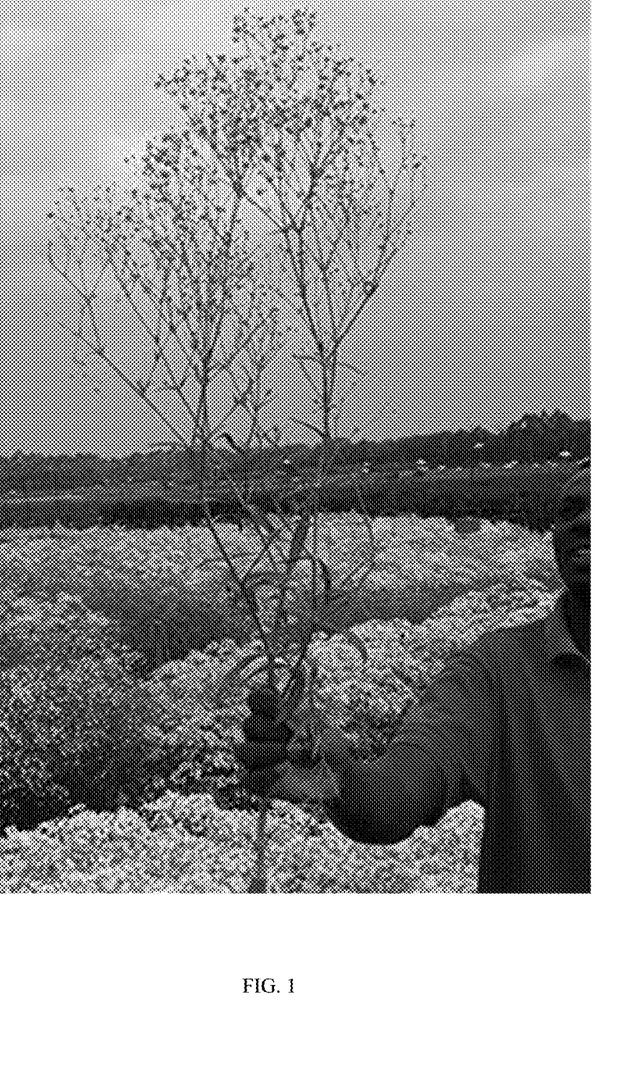
FIG. 1 illustrates in full color a typical inflorescence of 'DGYPSALBBF' grown outdoors in Kenya, directly after harvest in the field.
Figure 2:
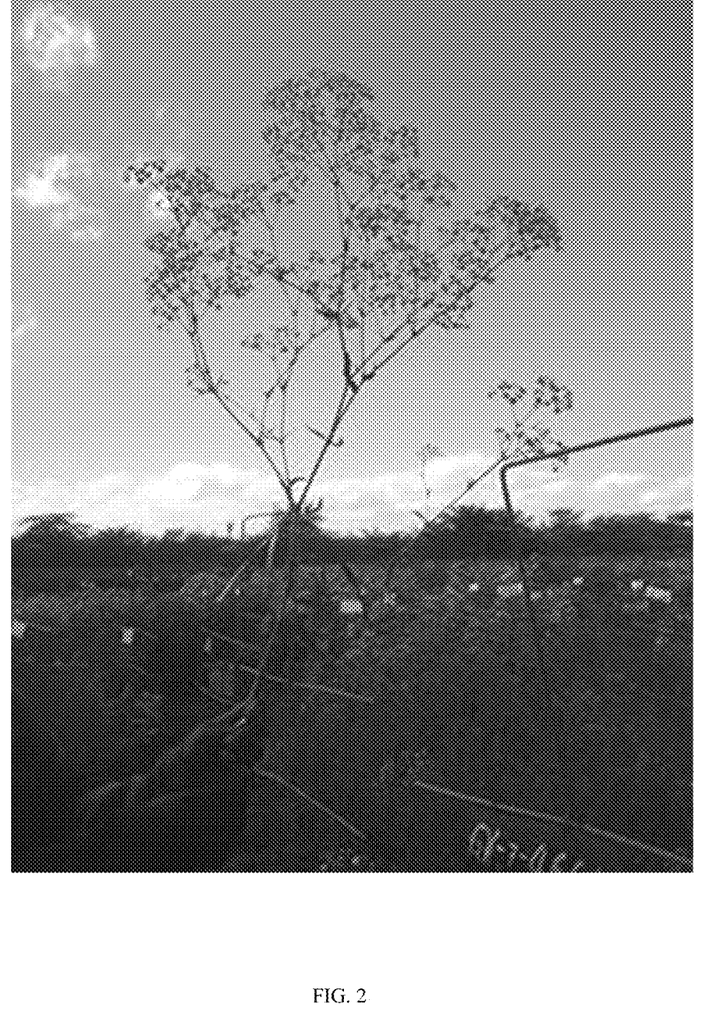
FIG. 2 illustrates in full color a typical inflorescence of the comparator 'DGYPXLENCE' grown outdoors in Kenya, directly after harvest in the same field.
Figure 3:
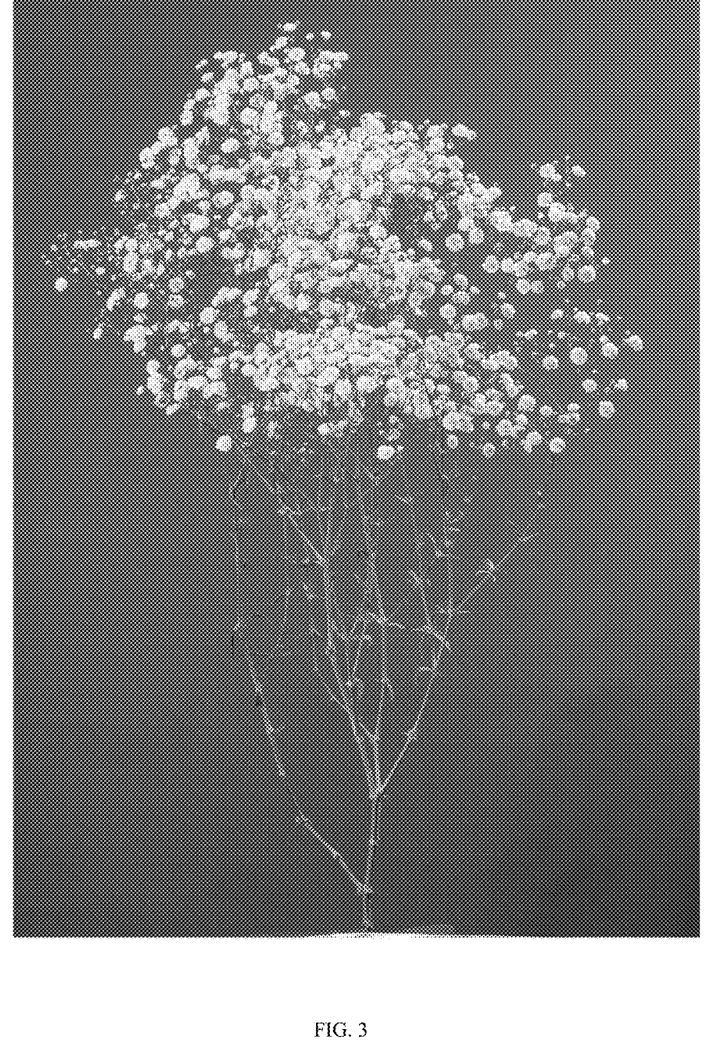
FIG. 3 illustrates in full color a typical inflorescence of 'DGYPSALBBF' grown outdoors in Israel.
Figure 4:
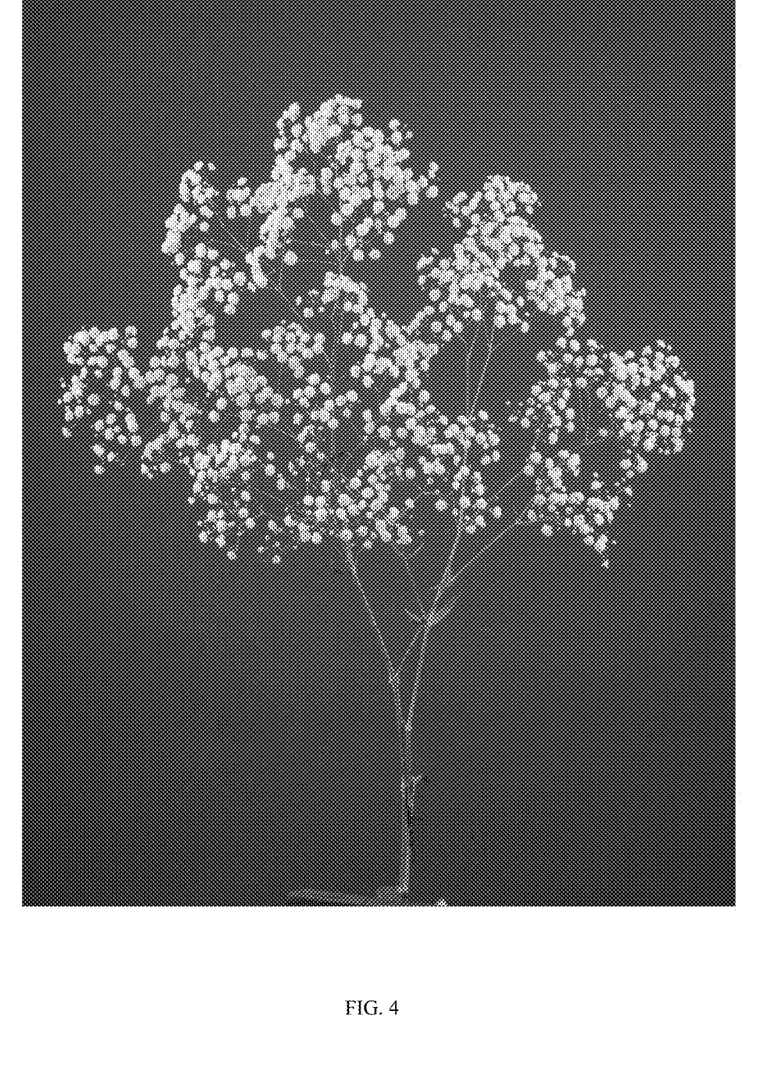
FIG. 4 illustrates a flowering stem of 'DGYPXLENCE' growth outdoors in Israel under the same conditions as 'DGYPSALBBF' illustrated in FIG. 3.
Figure 5:
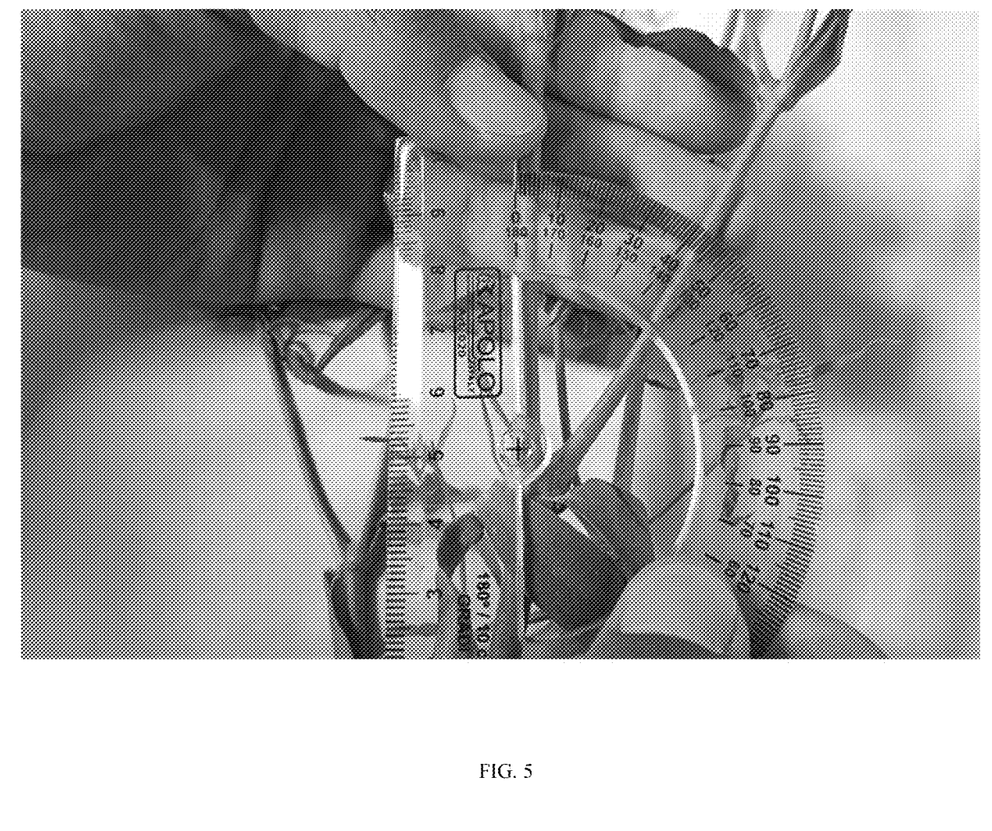
FIG. 5 illustrates a branch angle of 'DGYPSALBBF'.
Figure 6:
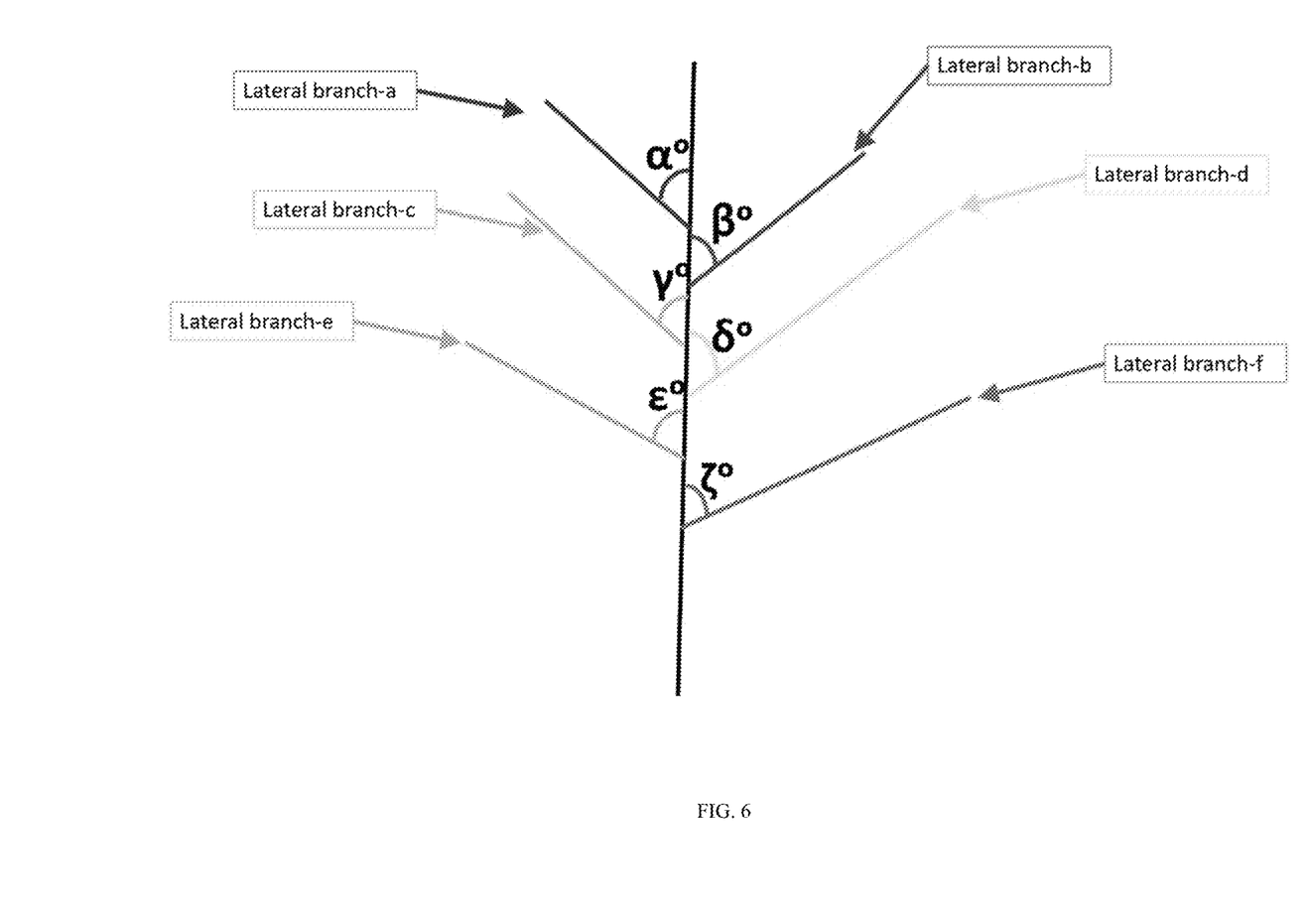
FIG. 6 is a diagram corresponding to branch data in Tables 1 through 4.

*Gypsophila paniculata* is a well-known plant in ornamental horticulture. The acute angle of inflorescence branching discovered and developed by the inventor is novel. Lateral branch data is provided in Table 1 below. Data in Tables 1 through 3 was taken from plants grown during confidential outdoor field trials in Ecuador FIG. 6 includes a diagram of the angles and branches described in Tables 1 through 3.

TABLE 1

'DGYPSALBBF'
Grown in Ecuador
Lateral Angle (°)

| plant no. | α | β | γ | δ | ε |
|---|---|---|---|---|---|
| 21 | 40 | 40 | 35 | 40 | 40 |
| 22 | 40 | 40 | 40 | 45 | |
| 23 | 40 | 40 | 40 | 35 | 40 |
| 24 | 40 | 40 | 30 | 40 | 40 |
| 25 | 40 | 50 | 40 | 40 | 40 |
| 26 | 45 | 40 | 40 | 40 | 45 |
| Average | 40.83 | 41.67 | 37.5 | 40 | 41 |

TABLE 2

'DGYPXLENCE'
Grown in Ecuador
Lateral Angle (°)

| plant no. | α | β | γ | δ | ε | ζ |
|---|---|---|---|---|---|---|
| 11 | 50 | 55 | 50 | 40 | 50 | |
| 12 | 55 | 55 | 50 | 45 | 50 | 50 |
| 13 | 40 | 45 | 60 | 50 | 45 | |
| 14 | 55 | 40 | 50 | 50 | 50 | |
| 15 | 55 | 50 | 45 | 45 | 50 | |
| 16 | 50 | 55 | 50 | 40 | 50 | |
| 17 | 45 | 50 | 40 | 50 | 50 | |
| 18 | 40 | 40 | 50 | 50 | 45 | 50 |
| 19 | 50 | 35 | 60 | 50 | 45 | |
| 20 | 45 | 40 | 50 | 50 | 50 | |
| Average | 48.5 | 46.5 | 50.5 | 47 | 48.5 | 50 |

TABLE 3

'DGYPCOSMIC'
Grown in Ecuador
Lateral Angle (°)

| plant no. | α | β | γ | δ | ε |
|---|---|---|---|---|---|
| 1 | 40 | 45 | 40 | 40 | |
| 2 | 40 | 40 | 40 | 40 | |
| 3 | 40 | 40 | 35 | 40 | 40 |
| 4 | 45 | 40 | 42 | 40 | |
| 5 | 40 | 50 | 40 | 40 | |
| 6 | 40 | 40 | 40 | 50 | 50 |
| 7 | 40 | 40 | 45 | 40 | |
| 8 | 40 | 45 | 40 | 40 | 40 |
| 9 | 38 | 40 | 40 | 38 | 40 |
| 10 | 35 | 40 | 50 | 38 | 40 |
| Average | 39.80 | 42 | 41.2 | 40.6 | 42 |

TABLE 4

| Consolidated Educator Trial | Average Lateral Angle (°) | | | Average length of lateral branch (cm) | | | | | Average (mm) |
|---|---|---|---|---|---|---|---|---|---|
| | γ | δ | ε | a | b | c | d | e | flower size |
| DGYPCOSMIC | 41.2 | 40.6 | 42 | 28.7 | 35 | 39.3 | 46.1 | | 9.53 |
| DGYPXLENCE | 50.5 | 47 | 48.5 | 31.5 | 36.5 | 43.8 | 47.7 | 48.75 | 10.55 |
| DGYPSALBBF | 37.5 | 40 | 41 | 36 | 40.67 | 42.83 | 50.67 | 55 | 11.8 |

Figure 7:
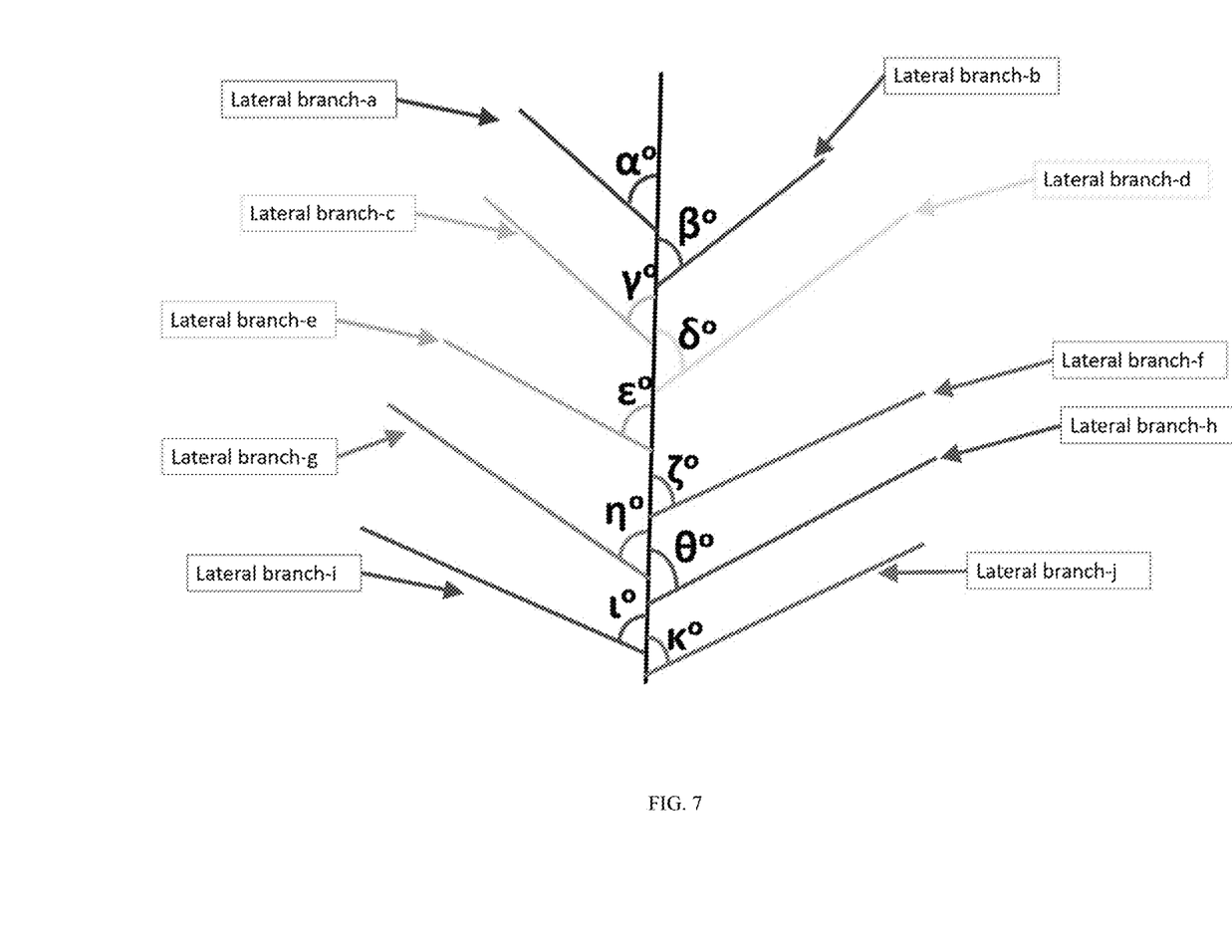
FIG. 7 is a diagram corresponding to branch data in Tables 5 through 7.
Figure 8:
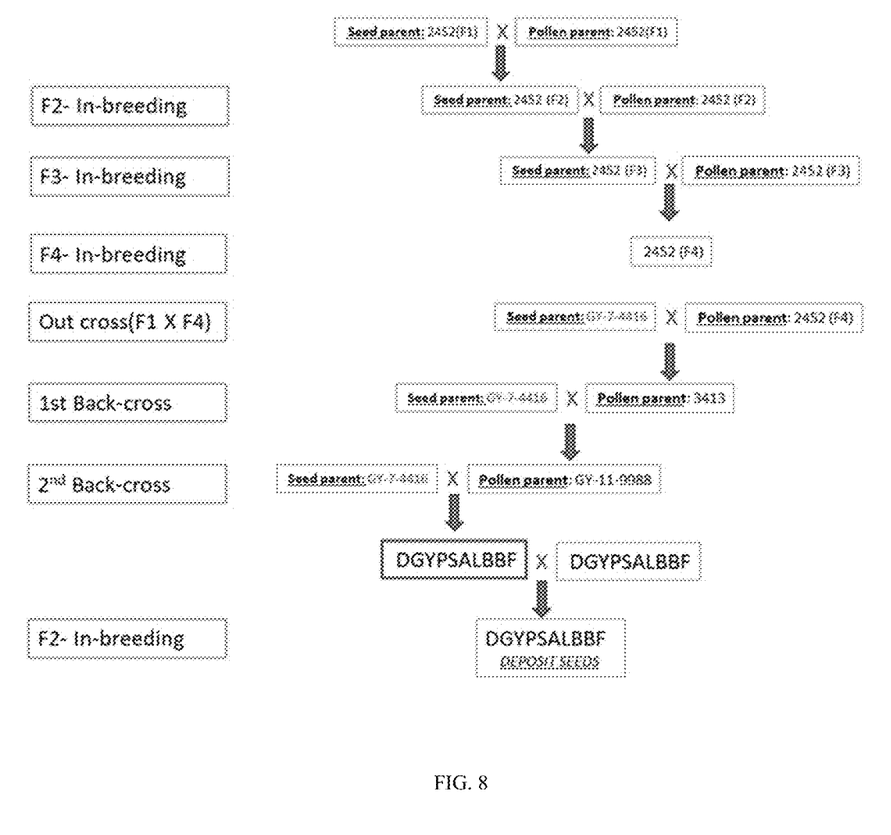
FIG. 8 is a diagram of the breeding scheme resulting in the *Gypsophila* variety 'DGYPSALBBF'.

Lateral branch data is provided in Table 1 below. Data in Tables 1 through 3 was taken from plants grown during confidential outdoor field trials in Ecuador FIG. 7 includes a diagram of the angles and branches described in Tables 5 through 7.

TABLE 5

'DGYPSALBBF' grown in Kenya Lateral Angle (°)

| plant no. | α | β | γ | δ | ε | ζ | η | θ | ι | κ |
|---|---|---|---|---|---|---|---|---|---|---|
| 11 | 40 | 35 | 40 | 35 | 35 | 45 | | | | |
| 12 | 40 | 35 | 35 | 45 | 35 | 40 | 40 | 35 | | |
| 13 | 45 | 45 | 30 | 35 | 35 | 35 | 40 | 30 | | |
| 14 | 40 | 40 | 45 | 35 | 40 | 35 | 40 | 35 | 40 | 40 |
| 15 | 50 | 45 | 50 | 45 | 45 | 40 | 50 | 40 | 35 | 30 |
| 16 | 45 | 45 | 40 | 40 | 40 | 35 | 30 | | | |
| 17 | 35 | 40 | 40 | 40 | 35 | 35 | 35 | | | |
| 18 | 40 | 40 | 45 | 30 | 40 | 35 | | | | |
| 19 | 40 | 45 | 40 | 35 | 35 | | | | | |
| 20 | 40 | 45 | 45 | 40 | 40 | 35 | | | | |
| Average | 41.5 | 41.5 | 41 | 38 | 38 | 37.2 | 39.2 | 35 | 37.5 | 35 |

TABLE 6

'DGYPXLENCE' grown in Kenya Lateral Angle (°)

| plant no. | α | β | γ | δ | ε | ζ | η | θ | ι | κ |
|---|---|---|---|---|---|---|---|---|---|---|
| 1 | 50 | 60 | 55 | 50 | 55 | 55 | 45 | 50 | 50 | 50 |
| 2 | 50 | 50 | 40 | 50 | 40 | 45 | 40 | 40 | 50 | 45 |
| 3 | 55 | 55 | 55 | 50 | 55 | 50 | 50 | 45 | 50 | 55 |
| 4 | 35 | 40 | 40 | 50 | 50 | 45 | 45 | 50 | 55 | |
| 5 | 50 | 50 | 50 | 40 | 55 | 50 | 50 | 45 | 50 | 50 |
| 6 | 45 | 50 | 50 | 50 | 50 | 50 | 45 | 50 | 50 | 45 |
| 7 | 60 | 60 | 60 | 55 | 45 | 45 | 55 | 50 | 50 | 45 |
| 8 | 45 | 50 | 55 | 55 | 55 | 55 | 55 | 60 | 60 | |
| 9 | 50 | 55 | 55 | 50 | 45 | 50 | 55 | 50 | 50 | |
| 10 | 45 | 55 | 55 | 50 | 50 | 45 | 50 | | | |
| Average | 48.5 | 52.5 | 51.5 | 50 | 50 | 49 | 49 | 48.9 | 51.7 | 48.3 |

TABLE 7

| Comparative | Average lateral angle (°) | | | | | | | | | |
|---|---|---|---|---|---|---|---|---|---|---|
| | α | β | γ | δ | ε | ζ | η | θ | ι | κ |
| DGYPXLENCE | 48.5 | 52.5 | 51.5 | 50 | 50 | 49 | 49 | 48.9 | 51.7 | 48.3 |
| DGYPSALBBF | 41.5 | 41.5 | 41 | 38 | 38 | 37.2 | 39.2 | 35 | 37.5 | 35 |

In addition to the acute angle of branching discovered and developed by the inventors, as a larger flower has also been observed. A trial conducted in Israel with results collected during January of 2021 is reported in Tables 8 through 12. Differences in the noted characteristics between varieties can be observed in the lack of overlap in the standard deviation trend.

TABLE 8

| | Averaged Lateral Angle (°) | | | | | | | | | |
|---|---|---|---|---|---|---|---|---|---|---|
| DANGYP39 | 51.00 | 56.30 | 54.60 | 55.90 | 55.20 | 54.00 | 56.80 | 53.10 | 51.50 | 53.10 |
| STD | 6.15 | 5.40 | 6.67 | 9.13 | 9.68 | 6.58 | 6.99 | 6.30 | 6.49 | 9.71 |
| DGYPCOSMIC | 56.70 | 53.90 | 58.60 | 59.90 | 57.10 | 57.60 | 53.90 | 54.10 | 51.30 | 54.60 |
| STD | 3.33 | 6.03 | 3.69 | 4.63 | 3.0 | 6.22 | 5.72 | 5.04 | 9.03 | 7.63 |
| DGYPXLENCE | 58.40 | 54.80 | 60.80 | 60.40 | 66.0 | 59.80 | 61.10 | 64.30 | 62.60 | 64.40 |
| STD | 9.26 | 6.81 | 5.85 | 7.00 | 7.06 | 3.91 | 4.91 | 6.60 | 7.23 | 3.98 |
| DGYPSALBBF | 43.90 | 44.90 | 47.70 | 47.50 | 44.20 | 44.40 | 43.90 | 41.80 | 42.80 | 44.50 |
| STD | 3.03 | 4.12 | 7.50 | 5.89 | 4.69 | 8.25 | 5.78 | 3.46 | 3.43 | 6.92 |

TABLE 9

| | Averaged Length of lateral branch (cm) | | | | | | | | | |
|---|---|---|---|---|---|---|---|---|---|---|
| DANGYP39 | 8.75 | 13.25 | 19.55 | 27.20 | 33.80 | 42.30 | 45.00 | 47.10 | 52.10 | 48.70 |
| STD | 3.63 | 5.76 | 7.85 | 10.73 | 11.75 | 14.81 | 13.74 | 10.76 | 10.66 | 17.75 |
| DGYPCOSMIC | 12.50 | 16.25 | 21.60 | 26.00 | 31.40 | 36.30 | 42.60 | 49.40 | 56.20 | 56.85 |
| STD | 1.49 | 1.70 | 1.76 | 2.53 | 3.3 | 3.27 | 4.11 | 8.60 | 13.67 | 18.07 |
| DGYPXLENCE | 11.10 | 14.95 | 18.85 | 24.15 | 28.3 | 33.95 | 39.10 | 45.25 | 53.85 | 55.90 |
| STD | 1.94 | 2.47 | 4.31 | 6.16 | 6.36 | 5.00 | 6.31 | 11.10 | 10.43 | 14.04 |
| DGYPSALBBF | 14.00 | 19.20 | 23.30 | 27.60 | 30.80 | 35.80 | 42.70 | 51.50 | 42.60 | 38.80 |
| STD | 2.45 | 3.55 | 4.57 | 4.35 | 5.01 | 7.27 | 10.67 | 8.67 | 12.28 | 15.08 |

TABLE 10

| | Averaged Stem-Lateral Branch Length Ratio | | | | | | | | | | |
|---|---|---|---|---|---|---|---|---|---|---|---|
| DANGYP39 | 97 | 0.09 | 0.14 | 0.20 | 0.28 | 0.35 | 0.44 | 0.46 | 0.49 | 0.54 | 0.50 |
| STD | 5.1424 | 0.04 | 0.06 | 0.08 | 0.11 | 0.12 | 0.15 | 0.14 | 0.11 | 0.12 | 0.18 |
| DGYPCOSMIC | 98.6 | 0.13 | 0.17 | 0.22 | 0.26 | 0.32 | 0.37 | 0.43 | 0.50 | 0.57 | 0.57 |
| STD | 5.13 | 0.02 | 0.02 | 0.02 | 0.03 | 0.0 | 0.04 | 0.04 | 0.08 | 0.13 | 0.18 |
| DGYPXLENCE | 95 | 0.12 | 0.16 | 0.20 | 0.26 | 0.3 | 0.36 | 0.41 | 0.48 | 0.57 | 0.59 |
| STD | 4.4472 | 0.02 | 0.03 | 0.04 | 0.07 | 0.07 | 0.06 | 0.07 | 0.12 | 0.12 | 0.16 |
| DGYPSALBBF | 58.6 | 0.24 | 0.33 | 0.40 | 0.48 | 0.53 | 0.62 | 0.74 | 0.89 | 0.73 | 0.67 |
| STD | 6.11 | 0.04 | 0.08 | 0.09 | 0.09 | 0.11 | 0.16 | 0.19 | 0.17 | 0.20 | 0.28 |

TABLE 11

| | Averaged Flower Diameter (mm) | | | | | | | | | |
|---|---|---|---|---|---|---|---|---|---|---|
| DANGYP39 | 10.00 | 9.70 | 10.0 | 10.0 | 9.90 | 9.90 | 9.60 | 8.90 | 9.55 | 9.80 |
| STD | 0.47 | 0.48 | 0.47 | 0.00 | 0.57 | 0.57 | 0.74 | 2.64 | 0.55 | 0.54 |
| DGYPCOSMIC | 10.00 | 9.65 | 9.70 | 9.75 | 9.65 | 9.80 | 9.60 | 9.30 | 9.15 | 9.45 |
| STD | 0.53 | 0.63 | 0.59 | 0.54 | 0.6 | 0.48 | 0.61 | 0.54 | 0.58 | 0.44 |
| DGYPXLENCE | 10.55 | 10.20 | 10.35 | 10.06 | 10.2 | 10.20 | 10.20 | 10.05 | 9.95 | 10.05 |
| STD | 0.64 | 0.59 | 0.58 | 0.58 | 0.58 | 0.54 | 0.54 | 0.69 | 0.60 | 0.60 |
| DGYPSALBBF | 12.15 | 12.50 | 12.05 | 12.15 | 12.15 | 12.05 | 12.05 | 12.15 | 12.20 | 12.15 |
| STD | 0.47 | 0.47 | 0.44 | 0.34 | 0.34 | 0.37 | 0.44 | 0.53 | 0.63 | 0.34 |

TABLE 12

| Variety | Consolidated Average Flower Diameter (mm) |
|---|---|
| DANGYP39 | 9.74 |
| STD | 0.34 |
| DGYPCOSMIC | 9.61 |
| STD | 0.25 |
| DGYPXLENCE | 10.18 |
| STD | 0.17 |
| DGYPSALBBF | 12.16 |
| STD | 0.13 |

Botanical Description

In the following description, color references are made to the Royal Horticultural Society Mini Colour Chart 2005 except where general terms of ordinary dictionary significance are used. The following observations and measurements describe 'DGYPSALBBF' plants grown in ground beds, outdoors in Moshav Mishmar Hashiva, Israel, under natural lighting. Measurements were taken during Spring and Summer. The growing temperature ranged from approximately 12° C. to 35° C. during the days, 4° C. to 28° C. during the nights. Measurements and numerical values represent averages of typical plant types.

Botanical classification: *Gypsophila paniculata* 'DGYPSALBBF'

Propagation

Time to Initiate Rooting: Vegetative cuttings
Root Description: 28 to 48 days at approximately 20° C.
Root Description: Fibrous.

Plant

Growth Habit: Upright.
Height: Approximately 100 cm
Plant Spread: Approximately 60 cm
Growth Rate: Approximately 16 weeks to begin harvesting flowering stems.
Branching Characteristics: Basal branch and side branches along the main branch.
Length of Lateral Branches: Approximately 34 cm.
Approximate Quantity of Lateral Branches: Approximately 13.
Diameter of Lateral Branches: Approximately 0.45 cm.
Texture of Lateral Branches: Smooth.
Lateral Branch Shape: Medium upward curvature.
Lateral Branch Strength: Strong and flexible.
Lateral Branch Color: Approximately Yellow-Green group, RHS 146-C.

Angle of branching: Acute. Lateral branches emerge from main stem in a sharp angel (between main stem and lateral branches), lateral branches are longer—creating a narrow and crowded cut flower stem.
Stem Weight: 63 grams.
Internode Length: Average 6.1 cm.
Number of Leaves per Lateral Branch: Average 28.6.
Age of Plant Described: Approximately 41 weeks from planting.

Foliage

Leaf:
   Arrangement: Opposite.
   Compound or single: Compound.
   Shape of blade: Acuminate.
   Average Length: 7.5 cm.
   Average Width: Approximately 1.0 cm.
   Apex: Sharply pointed, acuminate to acute.
   Base: Cuneate.
   Attachment: Sessile.
   Margin: Entire.
   Texture of top surface: Rough.
   Texture of bottom surface: Rough.
Color:
   Young foliage upper side: Near R.H.S. Green Group. 142-A
   Young foliage under side: Near R.H.S. Green Group. 141-D
   Mature foliage upper side: Near R.H.S. Green Group. 135-D
   Mature foliage under side: Near R.H.S. Yellow-Green Group. 144-C
   Venation:
   Type: Parallel.
   Venation color upper side: Indistinguishable from leaf blade.
   Venation color under side: Near R.H.S. Green Group. 142-D
   Durability of foliage to stresses: As common to *Gypsophila*.

Flower

Bloom Period:
   Natural Season: Spring to Summer. Long days over 14 hours.
   If applicable Greenhouse Production: Approximately 16 weeks
Inflorescence:
   Type: Thyrse.
   Height: Approximately 85 cm.
   Width: Approximately 30 cm.
   Quantity of flowers per inflorescence: Approximately 1200.
Bud:
   Bud shape: Oblate.
   Bud length: Approximately 0.1 cm.
   Bud diameter: Approximately 0.2 cm.
   Bud color: Near R.H.S. White Group 155-D.
   Base/calyx: Near R.H.S. Green group 134-B, upper section White Group 155-B.
Individual Flower:
   Shape: Round.
   Quantity of flowers and buds per plant: Approximately 12,000
   Diameter of entire flower: Approximately 12 mm.
   Depth of flower: Approximately 5 mm.
   Rate of opening: Individual flowers fully open approximately 5 days from the bud stage.
   Or if Cut Flower, longevity in vase: Approximately 14 days.
   Persistent or self-cleaning: Persistent
   Fragrance: Slight to moderate.
Petals:
   Length of petal: Approximately 5 mm.
   Width of petal: Approximately 1 mm.
   Apex: Truncate to retuse.
   Shape of petal: Spatulate.
   Petal margin: Entire.
   Petal Arrangement: Rosette.
   Petal Number: Approximately 80
   Petals Fused: At the very base.
   Petal Appearance: Matte.
   Petal Texture: Smooth.
Color:
   Upper surface at first opening: Near RHS White Group, 155-D.
   Upper surface at maturity: Near RHS White Group, 155-D.
   Upper surface at fading: Near RHS White Group, 155-D.
   Under surface at first opening: Near RHS White Group, 155-D.
   Under surface at maturity: Near RHS White Group, 155-D.
   Under surface at fading: Near RHS White Group, 155-C.
Petaloids or other Floral Structures: No.
Sepal:
   Number: 5
   Sepal Appearance: Matte.
   Sepal Arrangement: 2 whorls. (5 at external layer).
   Sepal length: Approximately 0.4 cm.
   Sepal width: Approximately 0.1 cm.
   Sepal shape: Lanceolate
   Base: Acute.
   Apex shape: Apiculate.
   Margin: Entire.
   Color: Near R.H.S. Green Group 134-B, transparent margins colored near White Group 155-C.
Peduncle:
   Length: Approximately 1.8 cm.
   Diameter: Approximately 0.8 cm.
   Angle: Approximately 50 degrees.
   Strength: Strong, flexible.
   Color: Near RHS Green Group, 134-A.
Pedicel:
   Length: Approximately 1.1 cm.
   Diameter: Approximately 0.04 cm.
   Angle: Approximately 35 degrees.
   Strength: Strong.
   Color: Near RHS Green Group, 140-A.

Reproductive Organs

Number of pistils per flower: 2.
Pistil Length: Approximately 0.12 cm.
Stigma shape: Indistinguishable from style.

Style color: Near RHS Red-Purple group 68A.
Style length: Approximately 0.1 cm.
Ovary Color: Near RHS Green 140-B
Stamens Quantity: Not observed.

Other Characteristics

Fruit/Seed Production: Color and shape of Fruits and Seeds: Kidney shape, Brown Group, N200-A.
Disease/Pest Resistance: Neither resistance nor susceptibility to normal diseases and pests of *Gypsophila* has been observed.
Drought Tolerance: Typical for *Gypsophila*.
Temperature Tolerance: USDA zones 3-9

We claim:

1. A plant of *Gypsophila* variety 'DGYPSALBBF', representative seed deposited at the NCIMB in Aberdeen, Scotland having deposit number NCIMB 43695.

2. A plant or a plant part thereof produced by growing the plant of claim 1, wherein the plant or plant part comprises at least one cell of *Gypsophila* 'DGYPSALBBF'.

3. A *Gypsophila* plant or part thereof, having all of the physiological and morphological characteristics of the plant of claim 1.

4. A tissue or cell culture of regenerable cells produced from the plant of claim 1.

5. The tissue or cell culture of claim 4, comprising tissues or cells from a plant part selected from the group consisting of leaves, vegetative cuttings, pollen, embryos, cotyledons, hypocotyl, meristematic cells, roots, root tips, pistils, anthers, flowers and stems.

6. A method of producing *Gypsophila* progeny comprising the steps of
    (a) crossing a plant of *Gypsophila* 'DGYPSALBBF' as a female or male parent with another *Gypsophila* plant, and (b) selecting progeny.

7. The method according to claim 6, wherein the second *Gypsophila* plant is another plant of *Gypsophila* 'DGYPSALBBF'.

8. A *Gypsophila* seed that produces the *Gypsophila* plant of claim 1.

9. A method for developing a *Gypsophila* plant in a plant breeding program using plant breeding techniques, applied to a pant of *Gypsophila* variety DGYPSALBBF' or a part thereof; the method comprising a technique selected from crossing, recurrent selection, backcrossing, pedigree breeding, market enhanced selection, haploid production, double haploid production, transformation, or mutation breeding, wherein said mutation breeding selects for a mutation that is spontaneously or naturally induced or artificially induced, thereby developing a *Gypsophila* plant derived from variety 'DGYPSALBBF'.

* * * * *